United States Patent
Davidson et al.

(10) Patent No.: US 7,634,305 B2
(45) Date of Patent: Dec. 15, 2009

(54) METHOD AND APPARATUS FOR SIZE ANALYSIS IN AN IN VIVO IMAGING SYSTEM

(75) Inventors: Tal Davidson, Haifa (IL); Arkady Glukhovsky, Santa Clarita, CA (US); Gavriel Meron, Petach Tikva (IL)

(73) Assignee: Given Imaging, Ltd., Yoqneam (IL)

( * ) Notice: Subject to any disclaimer, the term of this patent is extended or adjusted under 35 U.S.C. 154(b) by 878 days.

(21) Appl. No.: 10/736,738

(22) Filed: Dec. 17, 2003

(65) Prior Publication Data

US 2004/0127785 A1   Jul. 1, 2004

Related U.S. Application Data

(60) Provisional application No. 60/433,765, filed on Dec. 17, 2002.

(51) Int. Cl.
*A61B 5/00* (2006.01)

(52) U.S. Cl. .................. 600/424; 600/407; 600/438; 600/473; 600/476; 600/478; 600/102; 600/105; 600/109; 600/117; 600/118; 600/129; 600/178

(58) Field of Classification Search .............. 600/476, 600/160, 102, 105, 109, 117, 118, 129, 173, 600/178, 407, 424, 473, 478
See application file for complete search history.

(56) References Cited

U.S. PATENT DOCUMENTS

| | | | |
|---|---|---|---|
| 3,971,362 A | | 7/1976 | Pope et al. |
| 4,278,077 A | | 7/1981 | Mizumoto |
| 4,558,691 A | * | 12/1985 | Okada .................. 600/117 |
| 4,689,621 A | | 8/1987 | Kleinberg |
| 4,702,229 A | * | 10/1987 | Zobel .................. 600/117 |
| 4,844,076 A | | 7/1989 | Lesho et al. |
| 4,895,431 A | * | 1/1990 | Tsujiuchi et al. .............. 359/29 |
| H999 H | * | 12/1991 | Merkel et al. ............ 356/239.1 |
| 5,279,607 A | | 1/1994 | Schentag et al. |
| 5,604,531 A | * | 2/1997 | Iddan et al. .................. 348/76 |
| 5,690,108 A | * | 11/1997 | Chakeres .................... 600/424 |
| 5,819,736 A | | 10/1998 | Avny et al. |
| 5,920,995 A | * | 7/1999 | Sammut ...................... 42/122 |
| 5,967,968 A | * | 10/1999 | Nishioka .................... 600/117 |

(Continued)

FOREIGN PATENT DOCUMENTS

DE          34 40 177          5/1986

(Continued)

OTHER PUBLICATIONS

"Robots for the future"—Shin-ichi, et al., Nov. 29, 2001.

(Continued)

*Primary Examiner*—Brian Casler
*Assistant Examiner*—Baisakhi Roy
(74) *Attorney, Agent, or Firm*—Pearl Cohen Zedek Latzer, LLP

(57) ABSTRACT

A device, system and method for capturing in-vivo images allows for size or distance estimations for objects within the images. A scale may be overlayed on or otherwise added to the images and, based on a comparison between the scale and an image of an object, the size of the object and/or the distance of the object from an imaging device may be estimated or calculated.

24 Claims, 3 Drawing Sheets

U.S. PATENT DOCUMENTS

| | | | |
|---|---|---|---|
| 5,993,378 A | 11/1999 | Lemelson | |
| 6,032,374 A * | 3/2000 | Sammut | 42/122 |
| 6,240,312 B1 * | 5/2001 | Alfano et al. | 600/476 |
| 6,459,481 B1 * | 10/2002 | Schaack | 356/241.1 |
| 6,478,732 B2 * | 11/2002 | Adachi | 600/178 |
| 6,612,982 B1 * | 9/2003 | Ouchi | 600/139 |
| 6,947,043 B1 | 9/2005 | Klingman et al. | |
| 6,975,898 B2 * | 12/2005 | Seibel | 600/473 |
| 7,009,634 B2 * | 3/2006 | Iddan et al. | 348/76 |
| 7,366,995 B2 | 4/2008 | Montague | |
| 2001/0051766 A1 * | 12/2001 | Gazdzinski | 600/309 |
| 2002/0103417 A1 | 8/2002 | Gazdzinski | |
| 2002/0107444 A1 * | 8/2002 | Adler | 600/424 |
| 2002/0109774 A1 | 8/2002 | Meron et al. | |
| 2003/0032863 A1 * | 2/2003 | Kazakevich | 600/173 |
| 2003/0167000 A1 * | 9/2003 | Mullick et al. | 600/424 |
| 2004/0127785 A1 | 7/2004 | Davidson et al. | |
| 2004/0176684 A1 * | 9/2004 | Tabuchi et al. | 600/424 |
| 2005/0014995 A1 * | 1/2005 | Amundson et al. | 600/105 |
| 2007/0060798 A1 * | 3/2007 | Krupnik et al. | 600/300 |
| 2007/0073161 A1 * | 3/2007 | Davidson | 600/476 |

FOREIGN PATENT DOCUMENTS

| | | |
|---|---|---|
| DE | 3629435 | 3/1987 |
| EP | 0403399 | 12/1990 |
| JP | 59069721 | 4/1984 |
| JP | 4109927 | 4/1992 |
| JP | 4144533 | 5/1992 |
| JP | 5015515 | 1/1993 |
| JP | 2001224553 | 8/2001 |
| WO | WO 98/11816 | 3/1998 |
| WO | WO 01/08548 | 2/2001 |
| WO | WO 01/50941 | 7/2001 |
| WO | WO 01/65995 | 9/2001 |
| WO | WO 03/053241 | 7/2003 |

OTHER PUBLICATIONS

"The Radio Pill", Rowlands, et al., British Communications and Electronics, Aug. 1960, pp. 598-601.
"Video Camera to "TAKE" "—RF System lab, Dec. 25, 2001.
"Wellesley company sends body montiors into space"—Crum, Apr. 1998.
www.rfnorkia.com—NORIKA3, Dec. 24, 2001.
"Wireless transmission of a color television moving image from the stomach using a miniature CCD camera, light source and microwave transmitter." Swain CP, Gong F, Mills TN. Gastrointest Endosc 1997;45:AB40.
BBC News Online—"Pill camera to 'broadcast from the gut'", Feb. 21, 2000, www.news.bbc.co.uk.
Lewkowicz et al., "Calibration of Images of the Wireless Capsule Endoscope", Abstract, American College of Gastroenterology, 66$^{th}$ Annual Scientific Meeting, Las Vegas, NV, Oct. 19-23, 2001.
Paint Shop Pro Version 9, cited in an Office Action dated Jan. 22, 2009 for U.S. Appl. No. 11/518,523.

* cited by examiner

METHOD AND APPARATUS FOR SIZE ANALYSIS IN AN IN VIVO IMAGING SYSTEM

CROSS REFERENCE TO RELATED APPLICATIONS

This application claims benefit from prior provisional application Ser. No. 60/433,765 filed Dec. 17, 2002, entitled "METHOD AND APPARATUS FOR SIZE ANALYSIS IN AN IN VIVO IMAGING SYSTEM."

FIELD OF THE INVENTION

The present invention relates to an in-vivo device, system and method such as for imaging an in-vivo lumen; more specifically, to a method and apparatus in an in-vivo system for determining the size and/or distance of an in-vivo object.

BACKGROUND OF THE INVENTION

Devices and methods for performing in-vivo imaging of passages or cavities within a body are known in the art. They may include, for example, swallowable capsules which collect data and which may transmit the data to a receiver system. Such devices may also include, inter alia, various endoscopic imaging systems and devices for performing imaging in various internal body cavities.

An in-vivo imaging device may include, for example, an imaging system for obtaining images and other data from inside a body cavity or lumen, such as the gastrointestinal (GI) tract. The imaging system may include, for example, an illumination unit, such as a set of light emitting diodes (LEDs), or other suitable light sources. The device may include an imaging sensor and an optical system, which focuses the images onto the imaging sensor. A transmitter and antenna may be included for transmitting the image signals. A receiver/recorder, for example worn by the patient, may record and store image and other data. The recorded data may then be downloaded from the receiver/recorder to a computer or workstation for display and analysis.

Upon display or analysis of the images obtained from the device, it would be useful to be able to determine the size of objects viewed, such as for example tumors or polyps.

SUMMARY OF THE INVENTION

An embodiment of the device, system and method of the present invention enables the estimation or determination of the size of objects seen in in-vivo images from within body lumens or cavities, such as the gastrointestinal (GI) tract. According to an embodiment of the invention, calculations according to a certain algorithm(s) are performed on the images in order to present to an observer an estimation of the real size (or distances) of the objects in the image or provide an observer with a visual tool or guide aiding the observer in making such an estimation.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Embodiments of the system and method of the present invention may be used in conjunction with an imaging system or device such as embodiments described in U.S. Pat. No. 5,604,531 to Iddan et al. and/or in application number WO 01/65995 entitled "A Device And System For In-vivo Imaging", published on 13 Sep. 2001, both of which are hereby incorporated by reference. However, the device, system and method according to the present invention may be used with any suitable device, system and method providing imaging and other data from a body lumen or cavity.

Figure 1A:
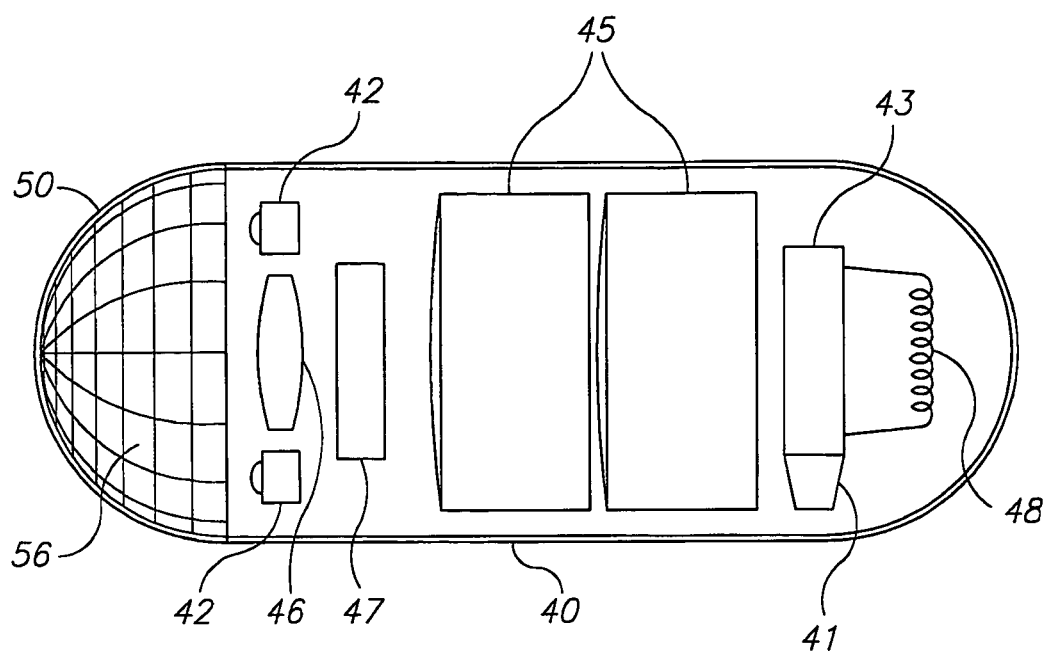
FIG. 1A shows a schematic diagram of an in-vivo imaging system according to one embodiment of the present invention.
Figure 1A:
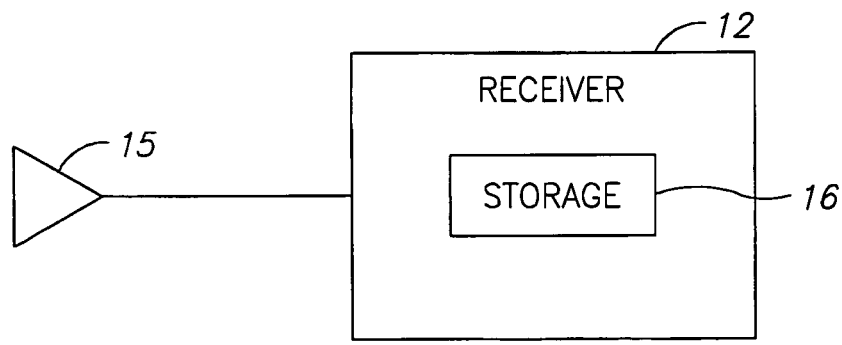
Figure 1A:
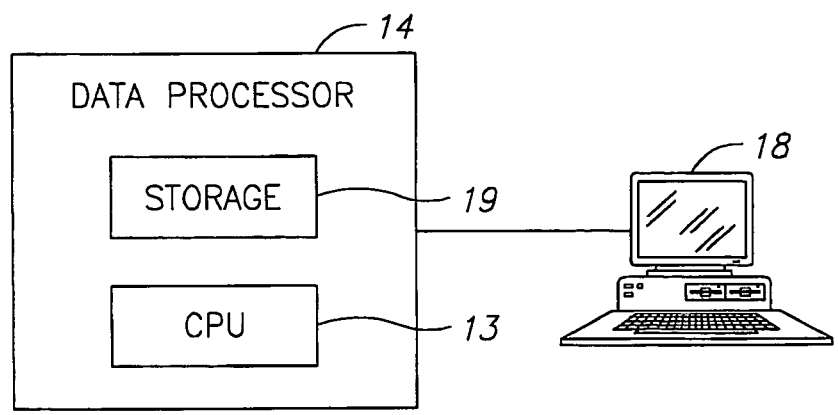

Reference is made to FIG. 1A, which shows a schematic diagram of an in-vivo imaging system according to one embodiment of the present invention. In an exemplary embodiment, a device 40 may be, for example, a swallowable capsule capturing images and possibly other data. Typically, device 40 is in the shape of a capsule, including at least one dome-shaped end 50; however, other shapes may be used, and the device need not be swallowable or a capsule. Typically, device 40 includes at least one sensor such as an imager 47, for capturing images, and a processing chip or circuit 41 that processes the signals generated by the imager 47. Processing circuit 41 need not be a separate component; for example, processing or a processing chip may be integral to the imager 47. An illumination device 42, such as a set of light emitting diodes (LEDs), or other suitable light sources, provides light to illuminate objects. An optical system, including, for example, one or more optical elements, such as one or more lenses 46 or composite lens assemblies (not shown), one or more suitable optical filters (not shown), or any other suitable optical elements (not shown), may aid in focusing reflected light onto the imager 47 and performing other light processing. Device 40 may be, for example, similar to embodiments described in U.S. Pat. No. 5,604,531 and/or WO 01/65995, described above. However, the device may be any sort of in-vivo sensor device and may have other configurations. For example, the device may be an endoscope.

Embodiments of the device are typically autonomous and are typically self-contained. For example, the device may be a capsule or other unit where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

According to one embodiment device 40 typically includes a transmitter 43, for transmitting image and other (e.g., non-image) information to a receiving device, and may include other components. The transmitter 43 is typically an ultra low power radio frequency (RF) transmitter with high bandwidth input, possibly provided in chip scale packaging, and may be combined with processing chip or circuit 41, as shown in FIG. 1A. The transmitter 43 may transmit via for example an antenna 48. The transmitter 43 may also act as a controller and include circuitry and functionality for controlling the device 40, although a separate control unit may be used. Typically, the device includes a power source 45, such as one or more batteries. For example, the power source 45 may include silver oxide batteries, lithium batteries, or other electrochemical cells having a high energy density, or the like. Other power sources may be used.

Other components and sets of components may be used. For example, the power source may be capable of receiving power from an external power source transmitting power to the device 40, and a controller separate from the transmitter 43 may be used.

In one embodiment, the imager 47 is a complementary metal oxide semiconductor (CMOS) imaging camera. The CMOS imager is typically an ultra low power imager and is provided in chip scale packaging (CSP). Other types of CMOS imagers may be used. In another embodiment, another imager may be used, such as a CCD imager, or another imager.

Preferably, located outside the patient's body in one or more locations, external to the in-vivo device 40, are a receiver 12, preferably including an antenna or antenna array 15, for receiving image and possibly other data from device 40, a receiver storage unit 16, for storing image and other data, a data processor 14, a data processor storage unit 19, and an image monitor 18, for displaying, inter alia, the images transmitted by the device 40 and recorded by the receiver 12. Typically, the receiver 12 and receiver storage unit 16 are small and portable, and are worn on the patient's body during recording of the images. Preferably, data processor 14, data processor storage unit 19 and monitor 18 are part of a personal computer or workstation, which includes standard components such as a processor or other controller 13, a memory (e.g., storage 19, or other memory), a disk drive, and input-output devices, although alternate configurations are possible. In alternate embodiments, the data reception and storage components may be of another configuration. In addition, a data decompression module for decompressing data may also be included.

The receiving and recording components may be, for example, similar to embodiments described in the above-mentioned U.S. Pat. No. 5,604,531 and/or WO 01/65995. However, the receiving and recording components may be of other suitable configurations and include other suitable functions.

It may be desired in such a system to capture via the optical system as great a viewing angle as possible. Typically, this may distort the image in such a way that the further an object from the center, the greater it is magnified; thus a distortion effect may be produced. Other distortion effects may be produced. For example, an object viewed at the edge of the display area may seem three (3) times as long as if it was seen at the center of the display area (other suitable distortion ratios may be used). This distortion ratio, e.g., the relative difference in size between an object at the center and a similarly sized object displaced from the center as a function of angular displacement of the object from the center of the dome, may be linear or non-linear, and may vary with different embodiments or different imaging systems. While for purposes of illustration, an example of a linear distortion ratio is provided, those of skill in the art will recognize that analogous calculations may be made in accordance with the present invention for other imaging systems. It should be emphasized that although the distortion of the optical system typically has radial symmetry, the present invention is not limited to this type of optical systems. It should further be emphasized that the present invention is not limited to in-vivo imaging systems having a dome-shaped window, but rather that the same principles described may be used with in-vivo systems having windows of another shape, such as a plane or a cone.

Figure 1B:
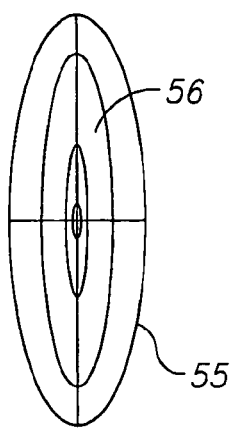
FIG. 1B is a perspective view of a lens, filter, or other device including a scale or other indication.

FIG. 1B is a perspective view of a lens, filter, or other device including a scale or other indication. Scale or indication 56 may be included in device or transparent piece 55 in various suitable known manners, such as printing, etching, raised or indented printing, etc.

Figure 2A:
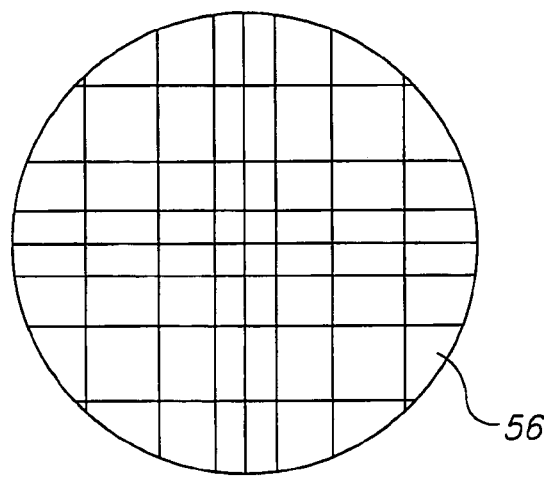
FIGS. 2A and 2B are examples of scales used with an in-vivo imaging system with a non-linear scale, reference frame, or other set of lines, bars, numbers, indicators, etc. overlaid or added to on an image in accordance with embodiments of the present invention.
Figure 2B:
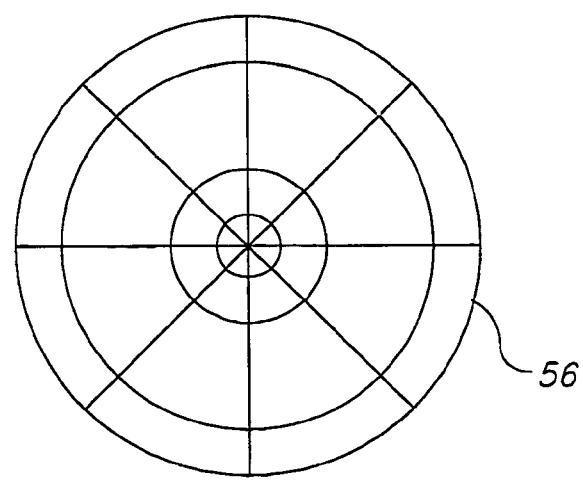

In accordance with one embodiment of the present invention, a scale such as scale 56 (FIG. 1A, FIG. 1B) may be overlaid or otherwise added to on the displayed image to give an estimate of the sizes of objects. Such a size estimate may be, for example, provided to a user at a processing and/or display system, may be produced by a user comparing an object to a scale, or by other methods. Various suitable scales such as reference frames or indications may be used, such as sets of lines, bars, numbers, indicators, etc. For example, a scale may be placed by drawing or etching it onto the dome or other transparent piece as shown in FIGS. 1A and 1B. Other devices may be used to add a scale to an image, such as a lens, filter, or other relatively clear device or transparent piece with a scale printed, etched or otherwise added to it, by adding such a scale to an imaging device, etc. In other embodiments, such a scale may be overlaid onto the image at any stage of the imaging process, for example, at the processing circuit 47, at processing circuits (e.g., CPUs, processors, specialized circuits, etc.) in other devices such as in the data processor 14, or at the monitor 18. Such digital addition of image elements to a video image is well known. The markings on the scale may be placed in accordance with the distortion pattern of the optics system used by a particular device. A set of reference lines on the scale may be, for example, orthogonal coordinate axes (e.g., cartesian coordinates), radial lines and concentric circles (e.g. polar coordinates), etc. If the scale is provided by the data processor 14 or at the monitor 18, in one embodiment the user may be able to toggle the scale on or off. FIG. 2A is an example of a scale, typically displayed on image monitor 18, of an in-vivo imaging system with a typically non-linear orthogonal scale overlaid on an image in accordance with an embodiment of the present invention. FIG. 2B is an example of a scale, typically displayed on image monitor 18, of an in-vivo imaging system with a typically non-linear polar scale overlaid on an image in accordance with an embodiment of the present invention. Scales 56 may have other suitable forms. It will be noted that in the example provided, markings at the outer portions of the viewing area are further apart than those at the center because the distortion particular to the embodiment shown magnifies images at the edge of the display relative to those at the center. Typically, an object measuring one unit at the edge of the viewing area should be roughly the size of one unit at the center. Other types of scales, indications or markings may be provided in accordance with various embodiments of the invention to provide a scale to a viewer, enabling the viewer to estimate the size of various objects seen. For example, a set of colors or shading gradients may be used. Numbers may be provided on the scale, providing estimates or ranges whereby the viewer may roughly estimate the size of viewed objects.

In another embodiment of the invention, the image may be digitally processed and altered in accordance with the distortion pattern of the optical system to compensate for the distortion. Upon displaying a digitally corrected view of an image, a linear measuring grid may be overlaid on the processed image.

The approximate size of an object can be determined by knowing the size of the dome of the device 40 and the illumination range of the illumination device. According to one embodiment, for example, the radius of the dome of an in-vivo imaging device is approximately 0.7 cm and the effective range of the illumination provided by an in-vivo device is approximately 3.0 cm. Moreover, a typical viewing angle may be approximately 110° to 140°. For purposes of illustration, a viewing angle of 120° is assumed. Thus, based on simple trigonometric calculations, the effective viewing diameter of circular images displayed may be calculated. For the example given, an object directly in front of the dome spanning the entire display would be approximately 2.4 cm, whereas an object at the maximum viewing distance that spans the entire display would be approximately 5.2 cm. While these figures, dimensions and distances may vary with different embodiments or different imaging systems, analogous calculations may be made for other imaging systems in accordance with embodiments of the present invention.

Thus, knowing, for example, the distortion ratio, maximum angle, and maximum and minimum distance of the optical system, a range of sizes may be assigned to an object filling some or all of the display or image based on its possible distance from the dome. Such ranges may be printed on a screen overlay. It will be clear to those of skill in the art that it is possible to calculate such a range of sizes for objects between the center and the edge of the viewing area based on simple principles of extrapolation for any optical distortion ratio, maximum angle, and maximum and minimum distance of the optical system. For many medical purposes, a range of sizes for an object such as provided by the above illustration may suffice. For example, the size of a polyp may correlate to the time until when it will turn cancerous. Knowledge of the size of a polyp therefore may enable a physician or other user of a system in accordance with the present invention to decide about urgency of the treatment, type of the treatment, and tools required for the treatment.

In addition, these estimates may be further refined based upon more specific knowledge of the distance of the object from the device 40. Various suitable methods of determining the distance or estimated distance of an object may be used. The known intensity of the illumination emanating from illumination device reflected by objects viewed correlates to their distance from the device. This intensity of reflected illumination may be measured by the data processor 14. Thus, for example, an object that reflects light only dimly is towards the far end of the illumination range, whereas an object that reflects light brightly is closer to the dome of the device. For the sake of simplicity, it may be assumed that the distance to an object is inversely proportional to its reflection coefficient. In one embodiment, such calculations can be based on the reflection coefficient or other known reflectance characteristics of the object being analyzed. For example, the user may indicate an object or class of objects (e.g., polyps), for which the data processor 14 has stored characteristics such as, for example, a known average reflectance, or the user may enter a certain reflectance. Such reflectance, combined with the known illumination intensity and possibly other information (transparency of GI fluids), may be used to calculate a distance or distance range. Other suitable characteristics may be used.

Such distance or distance range may be used to calculate the estimated size of the object. Based on this illustration, it will be clear to those of skill in the art that it is possible to calculate a range of sizes for objects based on the degree of reflection by an object of the illumination for any sort of objects whose illumination reflection characteristics are known. In accordance with embodiments of the invention, once the distance to the edges of an object have been calculated, its size may be determined by simple trigonometric calculations.

Size calculation may be performed manually, e.g., by having a user compare an object to a scale, or by a computing device, such as a controller within in-vivo device 40, or by, for example, components such as receiver 12, data processor 14, processor 13, etc. Other suitable components may perform such a calculation. An object to be sized may be determined automatically or may for example be selected by a user. A request for size estimate or analysis may be made by a user, or this may be done automatically. Object or pattern recognition techniques may be used to determine the shape or outline of an object. A user may indicate the outline of an object or an object itself. For example, a user may indicate two (or other numbers of) points on a monitor by, for example, using a pointing device to indicate coordinates on an image. For example, a user may select an image, and may move a pointing device such as a mouse over two or more points on an object, indicating, for example, a line to be sized (if two points are determined), or an outline of an image to be sized (if more points are determined). For example, by estimating a distance between a first point and a second point, the points generally corresponding to the largest visible dimension of an object, an estimate of the size of the object may be obtained.

Figure 3:
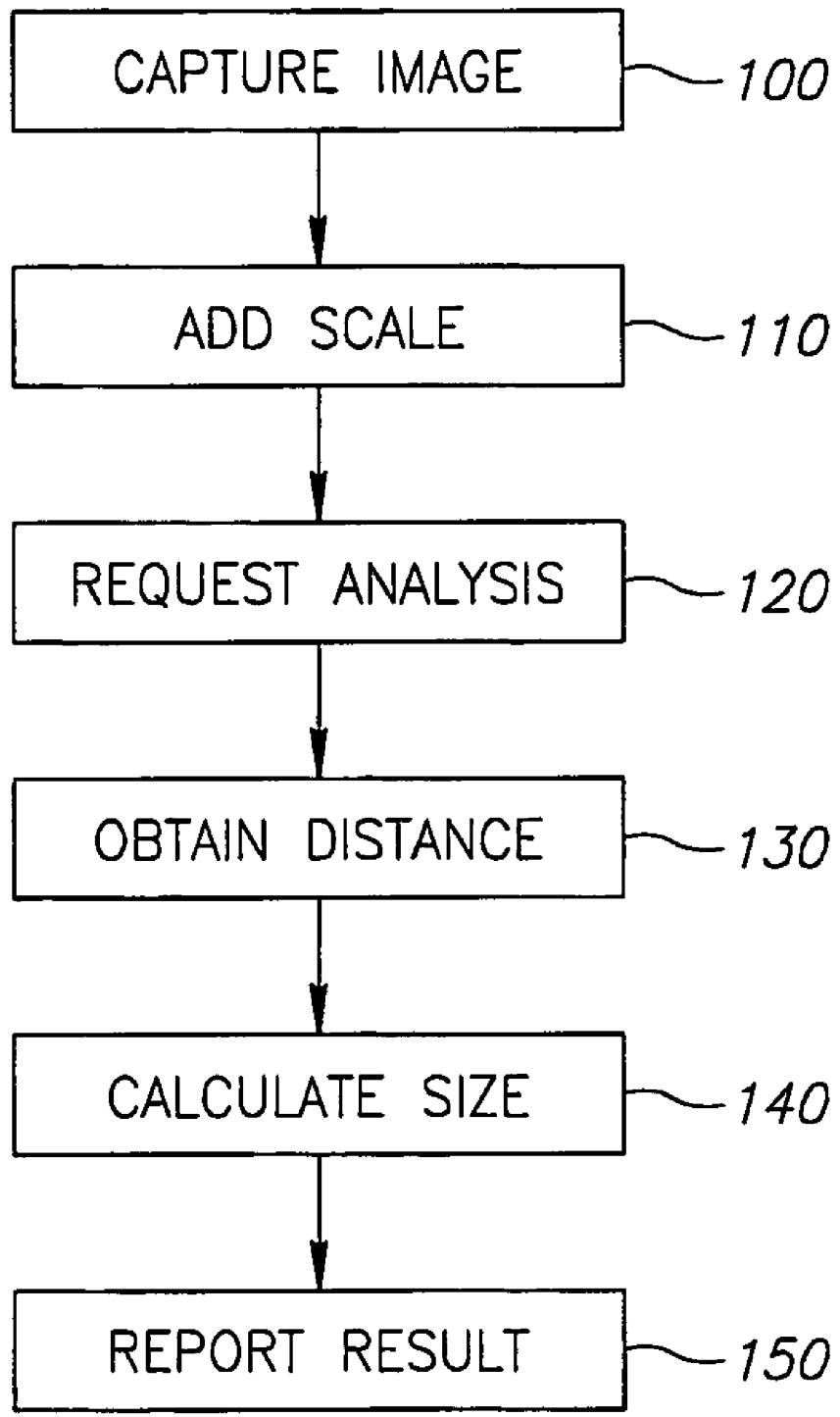
FIG. 3 depicts a series of steps of a method according to an embodiment of the present invention.

FIG. 3 depicts a series of steps of a method in accordance with an embodiment of the present invention. In step 100, an image is captured by an in-vivo imaging device.

In step 110, a scale or other indication may be added to or overlayed on the image. This may be done, for example, by imaging using a device including a scale (e.g., on a lens, on an optical dome, on a filter, on an imager, etc.), by adding the scale at a later point (e.g., by the imaging circuitry, by a post processing device), or by other methods. The scale or other indication may be added in an in-vivo device or, for example, at a processing device external to the in-vivo device (e.g., an external receiver, an external workstation, etc.).

In step 120, a request for size estimate or analysis may be made, for example, by the user's indicating two (or other numbers of points on a monitor or by the data processor using computer image analysis techniques. Such an explicit request need not be provided.

In step 130, the distance (or range of possible distances) may be analyzed or calculated, or otherwise obtained. Such distances may be determined beforehand—e.g., a fixed range of possible distances for any object imaged may be known or determined. In step 140, a size, distance or other result may be calculated. In step 150, an estimated size, distance or other result may be displayed or otherwise provided. Other steps or series of steps may be used. For example, an explicit size analysis need not be used—for example, a user may simply use a scale to estimate the size of an object.

The user of an in-vivo imaging system employing an embodiment of the present invention may, for example estimate the size of an object viewed on the monitor or other image display device. This measurement estimate may be made manually or automatically. For example, by comparing the dimensions of an object viewed on the monitor, and comparing to the gridlines, a user may estimate the size of the object. Alternately, this estimation may be performed automatically. A user may, for example, choose two points on the display (e.g., using a mouse or other user interface with the processing unit), possibly corresponding to the edges of an object, and the data processor 14 unit may provide a range of distances between the two points indicated, depending on the distance between the lens and the object (e.g., "The two points indicated are between 1.7 and 3.6 cm apart."). Other methods of inputting a user indication of an object and outputting a size or size range may be used. Alternately, the data processor 14 or other unit may choose an object or distance on an object, for example an object identified using computer image analysis techniques. This may be particularly useful for example where polyps of a certain size range (e.g., 0.5 mm to 1.5 mm) may be diagnosed differently from a polyp of a larger size range (e.g., 1 cm-3 cm). Thus, in this example, using an embodiment of the present invention, even a range of sizes may provide useful for diagnosing one type of polyp or another.

While the invention has been described with respect to a limited number of embodiments, it will be appreciated that many variations, modifications and other applications of the invention may be made. Embodiments of the present invention may include apparatuses for performing the calculations and operations herein. Such apparatuses may be specially constructed for the desired purposes or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as "estimating", "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

It will be appreciated by persons skilled in the art that the present invention is not limited to what has been particularly shown and described hereinabove. Rather the scope of the present invention is defined only by the claims, which follow:

What is claimed is:

1. A method for capturing in-vivo images, the method comprising:
    capturing an in-vivo image using an autonomous in vivo device, said device comprising a housing containing an imager, an optical system, an illumination device, a processor and a transmitter, wherein said image is captured with a distortion effect;
    digitally overlaying a non-linear scale on the in-vivo image in accordance with said distortion effect in order to enable a viewer to estimate the size of an object within the image.

2. The method of claim 1, comprising displaying the image.

3. The method of claim 1, wherein the step of overlaying the scale is performed at a processing device external to an in-vivo device.

4. The method of claim 1, wherein the steps of overlaying the scale and capturing the images are performed at an in-vivo device.

5. The method of claim 1, wherein the scale comprises a set of lines.

6. The method of claim 1, comprising providing a size estimate of an object contained in an image.

7. The method of claim 1, wherein said distortion effect is caused by said optical system.

8. The method of claim 1, wherein said step of digitally overlaying a non-linear scale on the in-vivo image comprises compensating for said distortion effect.

9. The method of claim 1, comprising estimating a distance between an in-vivo imaging device and an object in said in-vivo image.

10. The method of claim 1, comprising receiving a first point in said in-vivo image and a second point in said in-vivo image.

11. The method of claim 10, comprising calculating a distance between said first point and said second point.

12. The method of claim 10, comprising comparing an object in the image to the scale.

13. The method of claim 1, wherein said calculation is further based on a reflection coefficient of the object.

14. The method of claim 1, further comprising:
    measuring a reflected illumination intensity of the object; and
    correlating the reflected illumination intensity to a distance of the object from the device.

15. The method of claim 14, wherein the distance to the object is inversely proportional to its reflection coefficient.

16. The method of claim 1, wherein said calculation is further based on a transparency of GI fluids.

17. The method according to claim 1 further comprising refining the size calculation of the object based on a correlation between the intensity of reflected illumination and the distance of the object from the in vivo device.

18. The method according to claim 17 further comprising determining the distance of the object from the in vivo device based upon an inverse relationship to a reflection coefficient of the object.

19. An autonomous in-vivo imaging device comprising:
    an imager;
    an optical system;
    a transmitter;
    an illumination device; and
    a circuit to digitally overlay a non-linear scale onto images collected by the imager, wherein said images are captured with a distortion effect and said scale is digitally overlaid in accordance with said distortion effect to enable a viewer to calculate a size of an object within the image.

20. A system comprising:

an autonomous in-vivo device, said device comprising a housing containing an imager, an optical system, an illumination device and a transmitter; and a controller to:
- receive an image from said in-vivo device, wherein said image is captured with a distortion effect;
- digitally overlay a non-linear scale onto the image in accordance with said distortion effect to enable a viewer to calculate a size of an object within the image.

21. The system of claim 20, wherein the controller is to calculate an estimated size of objects in the image.

22. The system of claim 20, wherein the controller is to compare an object in the image to the scale.

23. The system of claim 20, wherein the controller is to receive a first point in an in-vivo image and a second point in said in-vivo image, and estimate a distance between the first point and the second point.

24. The system of claim 20, wherein the controller is to estimate a distance between the in-vivo imaging device and an object in said image.

* * * * *

UNITED STATES PATENT AND TRADEMARK OFFICE
CERTIFICATE OF CORRECTION

PATENT NO. : 7,634,305 B2  Page 1 of 1
APPLICATION NO. : 10/736738
DATED : December 15, 2009
INVENTOR(S) : Davidson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1391 days.

Signed and Sealed this

Twenty-first Day of December, 2010

David J. Kappos
*Director of the United States Patent and Trademark Office*